(12) United States Patent
Nagoshi

(10) Patent No.: US 9,182,356 B2
(45) Date of Patent: Nov. 10, 2015

(54) IMAGE PROCESSING APPARATUS

(71) Applicant: Keyence Corporation, Osaka (JP)

(72) Inventor: Keisuke Nagoshi, Osaka (JP)

(73) Assignee: Keyence Corporation, Osaka (JP)

( * ) Notice: Subject to any disclaimer, the term of this patent is extended or adjusted under 35 U.S.C. 154(b) by 438 days.

(21) Appl. No.: 13/654,732

(22) Filed: Oct. 18, 2012

(65) Prior Publication Data

US 2013/0128028 A1     May 23, 2013

(30) Foreign Application Priority Data

Nov. 22, 2011   (JP) ................................. 2011-254879

(51) Int. Cl.
| | |
|---|---|
| *H04N 7/18* | (2006.01) |
| *G01N 21/88* | (2006.01) |
| *G02B 7/08* | (2006.01) |
| *H04N 5/225* | (2006.01) |
| *H04N 5/232* | (2006.01) |

(52) U.S. Cl.
CPC .............. *G01N 21/8806* (2013.01); *G02B 7/08* (2013.01); *H04N 5/2256* (2013.01); *H04N 5/23212* (2013.01)

(58) Field of Classification Search
CPC .......................... H04N 5/2256; H04N 5/23212
USPC .................................................. 348/125–142
See application file for complete search history.

(56) References Cited

U.S. PATENT DOCUMENTS

| | | | |
|---|---|---|---|
| 4,556,907 A | | 12/1985 | Urata et al. |
| 4,618,938 A | * | 10/1986 | Sandland et al. ............. 382/148 |
| 5,003,400 A | * | 3/1991 | Murakami et al. ............ 348/347 |
| 6,526,232 B1 | * | 2/2003 | Mizumura ...................... 396/72 |
| 6,785,403 B1 | * | 8/2004 | Murakami et al. ............ 382/104 |
| 6,809,761 B1 | * | 10/2004 | Tamaru ....................... 348/229.1 |
| 2004/0120571 A1 | * | 6/2004 | Duvdevani et al. ........... 382/149 |
| 2013/0128027 A1 | | 5/2013 | Katsurada et al. |

FOREIGN PATENT DOCUMENTS

| | | |
|---|---|---|
| JP | 2006-184019 | 7/2006 |
| JP | 2008-298569 | 12/2008 |
| JP | 2009-053485 | 12/2009 |
| JP | 2010-239041 | 10/2010 |

* cited by examiner

*Primary Examiner* — Jamie Atala
*Assistant Examiner* — Masum Billah
(74) *Attorney, Agent, or Firm* — Kilyk & Bowersox, P.L.L.C.

(57) ABSTRACT

Provided is an image processing apparatus which can easily perform focus adjustment only by switching a program in accordance with a kind of an inspection object. The image processing apparatus according to the invention includes: an imaging unit for imaging a region including an inspection object; a focus adjustment mechanism; and a control unit for controlling a operation of the focus adjustment mechanism. A plurality of pieces of inspection condition data are set, the data being made up of a plurality of setting items including a focus position data. When the switching instruction from one inspection condition data to another inspection condition data is accepted, the operation of the focus adjustment mechanism is controlled based on focus position data included in another inspection condition data after switching.

8 Claims, 13 Drawing Sheets

FIG. 10

| PROGRAM 01 | | SETTING EXAMPLE |
|---|---|---|
| EXTERNAL OUTPUT 1-4 | ALLOCATION OF OUTPUT FUNCTION | DETECT/BUSY/ERROR_ALL/POSITION |
| TRIGGER RELATED | TRIGGER SYSTEM | INSIDE(PERIOD[50ms]) / OUTSIDE(DELAY[50ms]) |
| TRIGGER RELATED | INTERNAL TRIGGER PERIOD | 50ms |
| TRIGGER RELATED | IMAGING DELAY TIME | 10ms |
| IMAGING RELATED | BRIGHTNESS | 50 |
| IMAGING RELATED | MODE | NORMAL / HDR / Hi-Gain |
| IMAGING RELATED | INTERNAL ILLUMINATION | ON/OFF |
| IMAGING RELATED | AF ADJUSTMENT POSITION | 40 |
| IMAGING RELATED | ZOOM SETTING | NORMAL/2-FOLD ZOOM |
| IMAGING RELATED | MAXIMIZATION OF IMAGE TAKING RANGE | ON/OFF |
| IMAGING RELATED | IMAGE TAKING RANGE (CENTER COORDINATE, WIDTH, HEIGHT) | "(159.5, 119.5), (320.0, 240.0)" |
| IMAGING RELATED | IMAGE TAKING RANGE | ENTIRE RANGE/CUSTOM RANGE (CENTER COORDINATE [159.5:119.5], WIDTH[320.0], HEIGHT[240.0]) |
| COLOR FILTER | | RGB(OFF) |
| ILLUMINATION CORRECTION | VALID/INVALID | INVALID |
| ILLUMINATION CORRECTION | CORRECTED RANGE (CENTER COORDINATE, WIDTH, HEIGHT) | "(159.5, 119.5), (320.0, 240.0)" |
| ILLUMINATION CORRECTION | CORRECTION/NON-CORRECTION | VALID (CENTER COORDINATE[159.5:119.5], WIDTH[320.0], HEIGHT[240.0])/INVALID |
| MASTER IMAGE | MASTER IMAGE | |
| TOOL 00 | TOOL TYPE | CORRECT POSITION |
| TOOL 00 | TEMPLATE SHAPE | RECTANGLE |
| TOOL 00 | TEMPLATE POSITION (CENTER COORDINATE) | (159.5, 119.5) |
| TOOL 00 | TEMPLATE RANGE | (100.0, 100.0) |
| TOOL 00 | TEMPLATE RANGE | RECTANGLE (CENTER COORDINATE[159.5:119.5], WIDTH[100.0], HEIGHT[100.0]) |
| TOOL 00 | TEMPLATE ANGLE | 0 |
| TOOL 00 | MAXIMIZATION OF DETECTED RANGE | ON |
| TOOL 00 | DETECTED RANGE SHAPE | RECTANGLE |
| TOOL 00 | DETECTED RANGE POSITION (CENTER COORDINATE) | (159.5, 119.5) |
| TOOL 00 | DETECTED RANGE | (320.0, 240.0) |
| TOOL 00 | DETECTED RANGE | ENTIRE RANGE/RECTANGLE (CENTER COORDINATE [159.5:119.5], WIDTH[320.0], HEIGHT[240.0]) |
| TOOL 00 | THRESHOLD: DEGREE OF AGREEMENT | 70 |
| TOOL 00 | ROTATION ACCEPTABLE RANGE (LOWER LIMIT, UPPER LIMIT) | [-180, 180] |
| TOOL 01 | TOOL TYPE | EDGE DISCRIMINATION TOOL |
| TOOL 01 | TOOL NAME | SCREW EDGE |
| TOOL 01 | SEARCHING ACCURACY | ROBUST |
| TOOL 01 | TEMPLATE SHAPE | RECTANGLE |
| TOOL 01 | TEMPLATE POSITION (CENTER COORDINATE) | (159.5, 119.5) |
| TOOL 01 | TEMPLATE RANGE | (100.0, 100.0) |
| TOOL 01 | TEMPLATE RANGE | RECTANGLE (CENTER COORDINATE[159.5:119.5], WIDTH[100.0], HEIGHT[100.0]) |
| TOOL 01 | TEMPLATE ANGLE | 0 |
| TOOL 01 | MAXIMIZATION OF DETECTED RANGE | ON |
| TOOL 01 | DETECTED RANGE SHAPE | RECTANGLE |
| TOOL 01 | DETECTED RANGE POSITION (CENTER COORDINATE) | (159.5, 119.5) |
| TOOL 01 | DETECTED RANGE | (320.0, 240.0) |
| TOOL 01 | DETECTED RANGE | ENTIRE RANGE/RECTANGLE (CENTER COORDINATE [159.5:119.5], WIDTH[320.0], HEIGHT[240.0]) |
| TOOL 01 | THRESHOLD: DEGREE OF AGREEMENT | 70 |
| TOOL 01 | ROTATION ACCEPTABLE RANGE (LOWER LIMIT, UPPER LIMIT) | [-180, 180] |

FIG. 12

| PROGRAM 02 | | SETTING EXAMPLE |
|---|---|---|
| EXTERNAL OUTPUT 1-4 | ALLOCATION OF OUTPUT FUNCTION | DETECT/BUSY/ERROR_ALL/POSITION |
| TRIGGER RELATED | TRIGGER SYSTEM | INSIDE(PERIOD[50ms]) / OUTSIDE(DELAY[50ms]) |
| TRIGGER RELATED | INTERNAL TRIGGER PERIOD | 50ms |
| TRIGGER RELATED | IMAGING DELAY TIME | 10ms |
| IMAGING RELATED | BRIGHTNESS | 50 |
| IMAGING RELATED | MODE | NORMAL / HDR / Hi-Gain |
| IMAGING RELATED | INTERNAL ILLUMINATION | ON/OFF |
| IMAGING RELATED | AF ADJUSTMENT POSITION | 80 |
| IMAGING RELATED | ZOOM SETTING | NORMAL/2-FOLD ZOOM |
| IMAGING RELATED | MAXIMIZATION OF IMAGE TAKING RANGE | ON/OFF |
| IMAGING RELATED | IMAGE TAKING RANGE (CENTER COORDINATE, WIDTH, HEIGHT) | "(159.5, 119.5), (320.0, 240.0)" |
| IMAGING RELATED | IMAGE TAKING RANGE | ENTIRE RANGE/CUSTOM RANGE (CENTER COORDINATE [159.5:119.5], WIDTH[320.0], HEIGHT[240.0]) |
| COLOR FILTER | | RGB(OFF) |
| ILLUMINATION CORRECTION | VALID/INVALID | INVALID |
| ILLUMINATION CORRECTION | CORRECTED RANGE (CENTER COORDINATE, WIDTH, HEIGHT) | "(159.5, 119.5), (320.0, 240.0)" |
| ILLUMINATION CORRECTION | CORRECTION/NON-CORRECTION | VALID (CENTER COORDINATE[159.5:119.5], WIDTH[320.0], HEIGHT[240.0])/INVALID |
| MASTER IMAGE | MASTER IMAGE | |
| TOOL 00 | TOOL TYPE | COLOR AREA |
| TOOL 00 | TOOL NAME | |
| TOOL 00 | HI SET VALUE VALID/INVALID (UPPER LIMIT) | INVALID |
| TOOL 00 | THRESHOLD: SET VALUE (LO, HI) | [50, 150] |
| TOOL 00 | EXTRACTED POSITION | (30, 60) |
| TOOL 00 | AREA | 56 |
| TOOL 00 | THRESHOLD (LOWER LIMIT, UPPER LIMIT) | H[0, 255] S[0, 255] V[0, 255] |

IMAGE PROCESSING APPARATUS

CROSS-REFERENCE TO RELATED APPLICATIONS

The present application claims foreign priority based on Japanese Patent Application No. 2011-254879, filed Nov. 22, 2011, the contents of which is incorporated herein by reference.

BACKGROUND OF THE INVENTION

1. Field of the Invention

The present invention relates to an image processing apparatus capable of switching a program in accordance with a kind of an inspection object, and performing focus adjustment in a relatively short period of time at the time of switching.

2. Description of Related Art

In the case of inspecting whether or not a defect is present in an inspection object, an appearance of the inspection object is imaged with an imaging device, to determine presence or absence of a defect based on the imaged image. In order to determine the presence or absence of the defect properly, the imaged image is required to be clear, and normally, focus adjustment is manually performed to image the inspection object.

In the case of manually performing focus adjustment, focus adjustment needs to be re-performed every time the kind of the inspection object flowing along a manufacturing line changes. In order to avoid such a complicated operation, for example, Japanese Unexamined Patent Publication No. 2006-184019 discloses a visual inspection device capable of performing focal point adjustment (focus adjustment) in accordance with a thickness and a height of an inspection target (inspection object). Accordingly, the thickness and the height of the inspection object change with a change in kind thereof, and even when a size of the inspection target in an imaging direction (distance from the imaging device) fluctuates, it is not necessary to manually perform focus adjustment.

However, when the visual inspection device disclosed in Japanese Unexamined Patent Publication No. 2006-184019 is adopted to the image processing sensor provided on the manufacturing line where a wide variety of inspection objects flow, focal point adjustment (focus adjustment) is performed every time the thickness and the height of the inspection target (inspection object) change, which has caused a problem of shortening the life of a focus adjustment mechanism. Naturally, this can be dealt with by changing the kind of the inspection object once in a given period. However, the focus adjustment operation requires a given period of time whether it is performed manually or automatically, thus making it difficult to reduce inspection cycle time.

SUMMARY OF THE INVENTION

The present invention has been made in view of such circumstances, and an object thereof is to provide an image processing apparatus which can easily perform focus adjustment only by switching a program in accordance with a kind of an inspection object.

In order to achieve the above object, according to one embodiment of the invention, an image processing apparatus includes: an imaging unit (an imaging portion) for imaging an imaged region including an inspection object; a focus adjustment mechanism for adjusting a focus position of the on the inspection object; and a control unit (a control portion) for controlling a operation (motion) of the focus adjustment mechanism, wherein the apparatus includes: an inspection condition data setting portion for setting a plurality of pieces of inspection condition data made up of a plurality of setting items including focus position data indicating a focalized position and concerning a condition for detecting the inspection object, and an inspection condition switching instruction accepting portion for accepting a switching instruction from one inspection condition data to another inspection condition data, and when the switching instruction for the inspection condition data is accepted, the control unit controls the operation of the focus adjustment mechanism based on focus position data included in another inspection condition data after switching.

In the first aspect, a plurality of pieces of inspection condition data are set, the data being made up of a plurality of setting items including a focus position data that indicates a focalized position and concerning a condition for detecting the inspection object.

The switching instruction from one inspection condition data to another inspection condition data is accepted, and when the switching instruction for the inspection condition data is accepted, the operation of the focus adjustment mechanism is controlled based on focus position data included in another inspection condition data after switching. It is possible to perform focus adjustment only by switching the inspection condition data, made up of a plurality of setting items including focus position data, by the switching instruction for the inspection condition data. Thus, the need for performing focus adjustment while changing the kind of the inspection object flowing along the manufacturing line once in a given period is eliminated, and furthermore focus adjustment can be performed in a relatively short period of time.

Further, according to another embodiment of the invention, the image processing apparatus according to the first aspect is provided with a switching portion for switching between whether to execute processing for setting the inspection condition data or to execute processing for determining failure/non-failure of the inspection object.

In the second aspect, since switching can be made between whether to execute processing for setting the inspection condition data or to execute processing for determining failure/non-failure of the inspection object, the need for performing focus adjustment every time the inspection is performed is eliminated by previously storing focus position data. Moreover, this allows easy diversion of focus position data to another image processing sensor.

Further, according to still another embodiment of the invention, in the image processing apparatus according to the second aspect, the inspection condition data setting portion accepts an input from the user to set focus position data when switching is performed so as to execute the processing for determining failure/non-failure of the inspection object, and the control unit controls the operation of the focus adjustment mechanism so that the focus position becomes a position corresponding to the focus position data included in another inspection condition data after switching when switching is performed so as to execute the processing for setting the inspection condition data.

In the third aspect, when switching is performed so as to execute the processing for determining failure/non-failure of the inspection object, an input from the user is accepted, to set focus position data. When switching is performed so as to execute the processing for setting the inspection condition data, the operation of the focus adjustment mechanism is controlled so that the focus position becomes a position corresponding to the focus position data included in another inspection condition data after switching. Hence, it is possible to adjust the focus position so as to become a position corresponding to the focus position data included in another inspection condition data after switching only by setting the inspection condition data, made up of a plurality of setting items including focus position data, thereby eliminating the need for performing focus adjustment every time the inspection is performed, and allowing easy diversion of the focus position data to another image processing apparatus.

Further, according to still another embodiment of the invention, in the image processing apparatus according to any one of the first to third aspects, when the switching instruction for the inspection condition data is accepted in the inspection condition switching instruction accepting portion, the control unit performs control so as not to change the focus position.

In the fourth aspect, even when the switching instruction for the inspection condition data is accepted, control is performed so as not to change the focus position, and when the inspection object can be inspected without trouble even if the image is slightly blurred due to displacement of a focal point, unnecessary focus adjustment is not required, and the life of the focus adjustment mechanism can be extended.

Further, according to still another embodiment of the invention, in the image processing apparatus according to any one of the first to fourth aspects, the focus adjustment mechanism is configured by a motor and a screw mechanism interlocked with the rotation of the motor.

In the fifth aspect, since the focus adjustment mechanism is configured by a motor and a screw mechanism interlocked with the rotation of the motor, the rotation of the motor is controlled so as to easily perform focus adjustment.

Further, according to still another embodiment of the invention, in the image processing apparatus according to the fifth aspect, when the switching instruction for the inspection condition data is accepted in the inspection condition switching instruction accepting portion, the control unit returns the focus position to the origin point and controls the rotation of the motor in accordance with the accepted switching instruction.

In the sixth aspect, when the switching instruction for the inspection condition data is accepted, the focus position is returned to the origin point, and the rotation of the motor is controlled in accordance with the accepted switching instruction. Accordingly, image processing for specifying the focus position is not required in the case of switching the inspection condition data, and the focus position can be adjusted based on the focus position data only by operation of the focus adjustment mechanism. Further, since the focus position has certainly been returned to the origin point, it is possible to prevent a loss of synchronization caused by successive focus adjustment.

Further, according to still another embodiment of the invention, in the image processing apparatus according to the sixth aspect, the inspection condition data includes information for correcting the origin point.

In the seventh aspect, since the inspection condition data includes information for correcting the origin point, a focus position can be more accurately adjusted based on the focus position data.

Further, according to still another embodiment of the invention, in the image processing apparatus according to any one of the first to seventh aspects, a typical image of the inspection object to become a reference for comparison with the inspection object is previously stored as a master image, and the inspection condition data is set while the master image is displayed.

In the eighth aspect, a typical image of the inspection object to become a reference for comparison with the inspection object is previously stored as a master image, and the inspection condition data is set while the master image is displayed. Accordingly, the user can set the inspection condition data while viewing the setting.

In the present invention, it is possible to perform focus adjustment only by switching inspection condition data, made up of a plurality of setting items including focus position data, by a switching instruction for the inspection condition data. Accordingly, focus adjustment while changing the kind of the inspection object flowing along the manufacturing line once in a given period is not required, and focus adjustment can be performed in a relatively short period of time.

BRIEF DESCRIPTION OF THE DRAWINGS

FIG. 10 is a table showing a list of inspection condition data for a positional correction tool and an edge discrimination tool;

FIG. 12 is a table showing a list of inspection condition data of a color area tool;

DETAILED DESCRIPTION OF PREFERRED EMBODIMENTS

Figure 1:
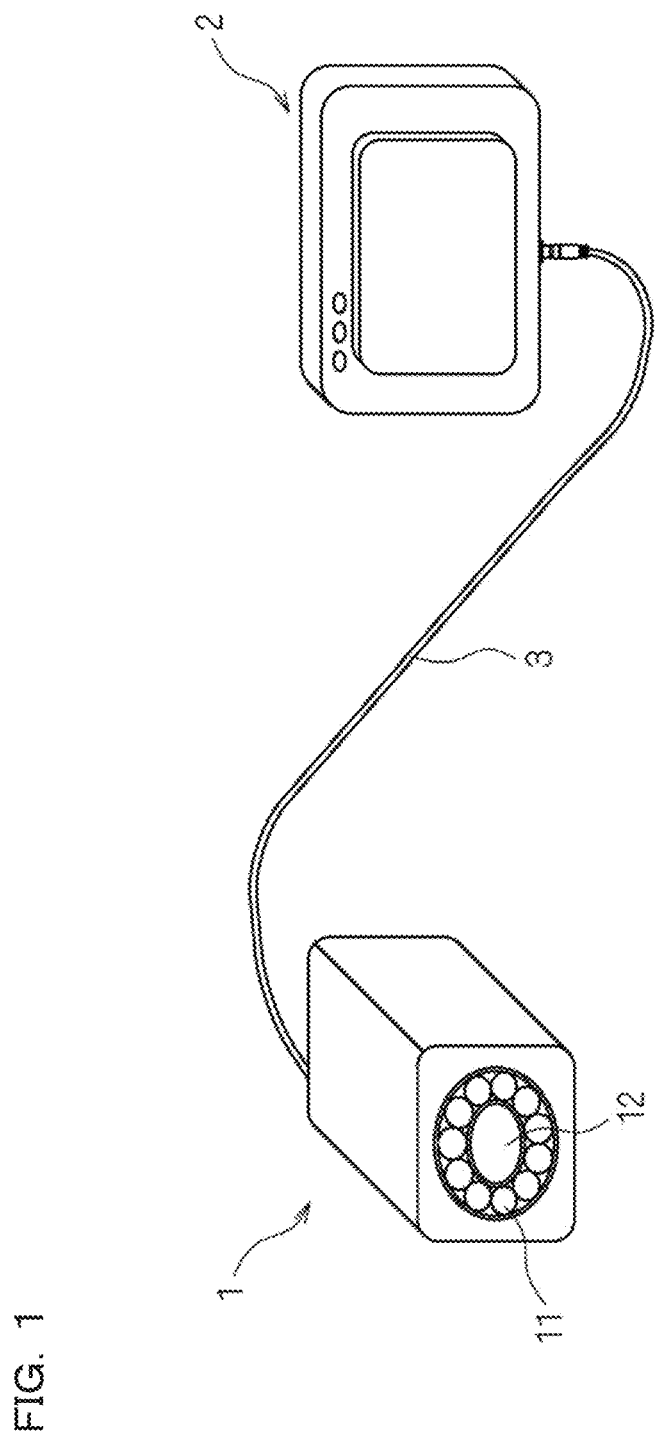
FIG. 1 is a schematic view showing a configuration of an image processing sensor according to an embodiment of the present invention.

Hereinafter, an image processing apparatus according to an embodiment of the present invention will be described with reference to the drawings. It is to be noted that elements having the same or similar configurations or functions throughout the drawings referenced in descriptions of the present embodiment are provided with the same or similar reference numerals, and detailed descriptions thereof are omitted. Hereinafter, descriptions will be given, taking as an example an image processing sensor as an image processing apparatus.

FIG. 1 is a schematic view showing a configuration of an image processing sensor according to an embodiment of the present invention. As shown in FIG. 1, the image processing sensor according to the present embodiment is configured by an imaging device 1 and a display device 2 connected with the imaging device 1 through a connection cable 3 in a data communicable manner.

Needless to say, the image processing sensor may be an external computer having a display in place of the display device 2. The imaging device 1 and the display device 2 may be integrally formed.

The imaging device 1 includes therein an FPGA, DSP, and the like which execute image processing, and includes a camera module ( ) having an imaging element for imaging an inspection object, and an illumination part for irradiating the inspection object with light. In order to make the imaging device 1 compact, for example, as shown in FIG. 1, a lens 12 is arranged close to the center of the front face of the imaging device 1, and a plurality of LEDs 11 are arranged as the illumination part so as to surround the periphery of the lens 12. It is to be noted that external illumination (ring illumination, or the like) may be provided separately from the imaging device 1

Figure 2A:
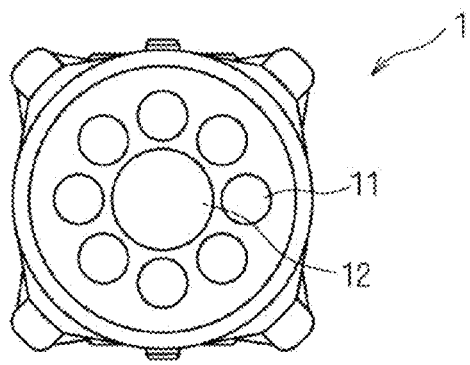
FIGS. 2A to 2C are outline views showing a configuration of an imaging device of the image processing sensor according to the embodiment of the present invention.
Figure 2B:
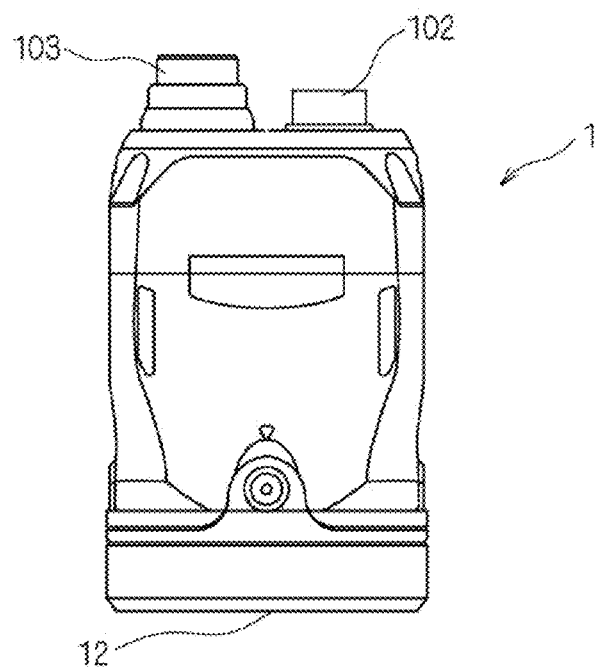
Figure 2C:
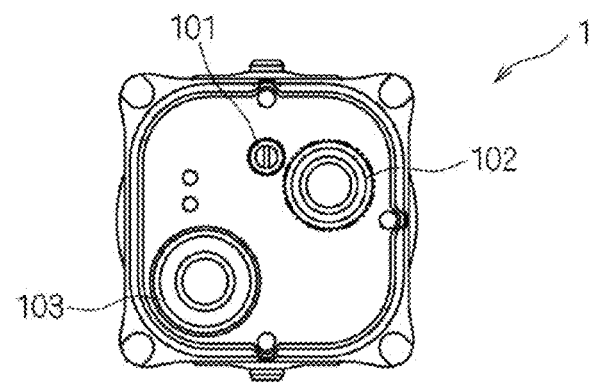

FIGS. 2A to 2C are outline views showing a configuration of the imaging device 1 of the image processing sensor according to the embodiment of the present invention. FIG. 2A is a front view showing the configuration of the imaging device 1 of the image processing sensor according to the embodiment of the present invention, FIG. 2B is a plan view showing the configuration of the imaging device 1 of the image processing sensor according to the embodiment of the present invention, and FIG. 2C is a rear view showing the configuration of the imaging device 1 of the image processing sensor according to the embodiment of the present invention.

As shown in FIG. 2A, the lens 12 is arranged close to the center of the front face of the imaging device 1, and the plurality of LEDs 11 are arranged so as to surround the periphery of the lens 12. At the time of imaging, the plurality of LEDs 11 are turned on, to irradiate the inspection object with light, thereby allowing clear imaging of the inspection object.

As shown in FIGS. 2B and 2C, the imaging device 1 includes, on its rear face, a power source connector 102 to be connected with a power cable that receives supply of electric power from an external power source, and a connection connector 103 connectable with the connection cable 3 that performs data communication with the display device 2. Further, the imaging device 1 also includes, on the rear face, a focus adjusting screw 101 capable of manually adjusting a focus.

Figure 3:
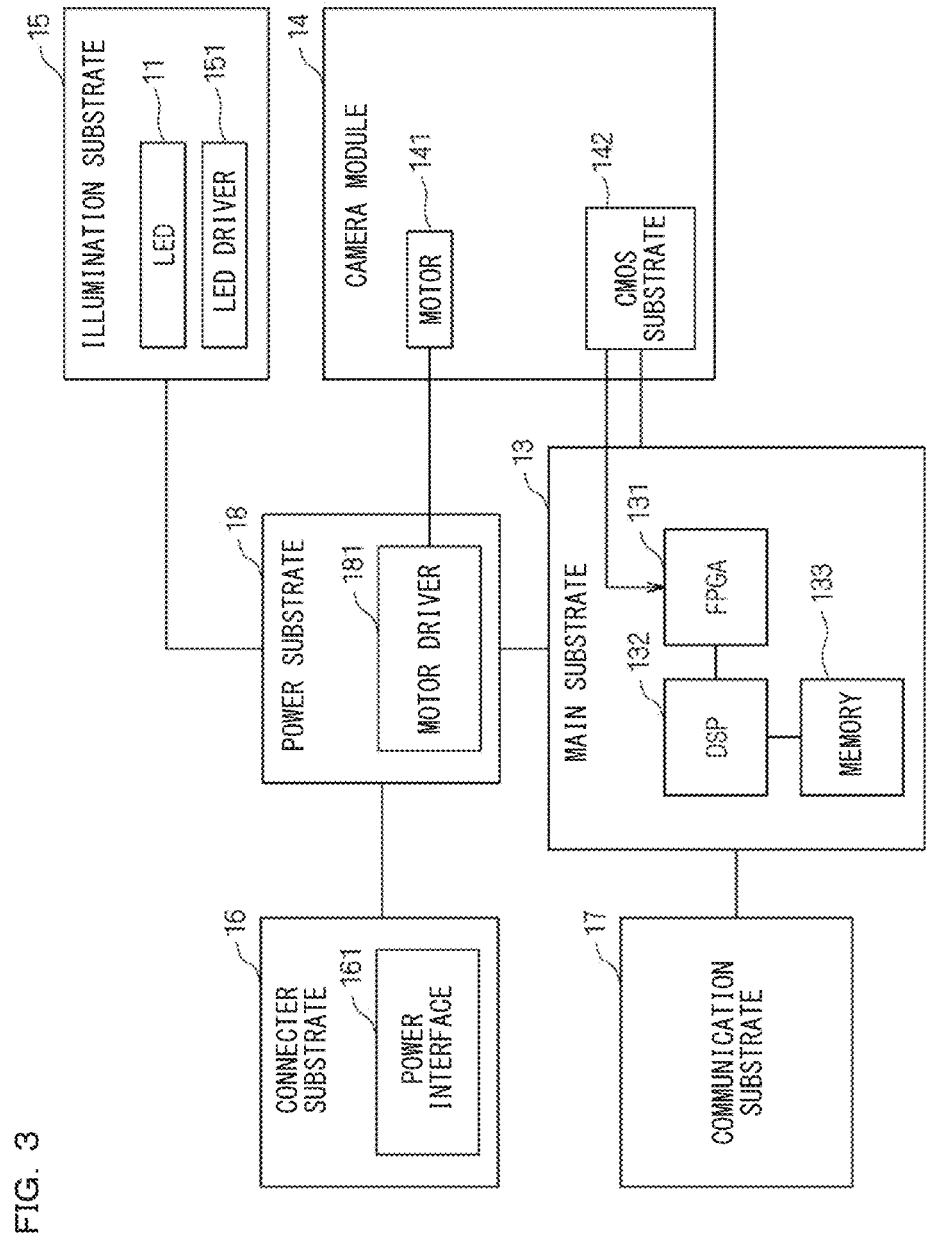
FIG. 3 is a block diagram showing a hardware configuration of the imaging device of the image processing sensor according to the embodiment of the present invention.

FIG. 3 is a block diagram showing a hardware configuration of the imaging device 1 of the image processing sensor according to the embodiment of the present invention. In FIG. 3, a connector substrate 16 receives supply of electric power from the external power source via the power source connector 102 (see FIGS. 2B and 2C) provided in a power interface 161. A power substrate 18 supplies the supplied electric power to each substrate. In the present embodiment, electric power is supplied to a camera module 14 via a main substrate 13.

A motor driver 181 of the power substrate 18 supplies drive electric power to a motor 141 of the camera module 14, to realize auto focusing.

A communication substrate 17 transmits to the display device 2 an OK/NG signal (determination signal) outputted from the main substrate 13 and indicating failure/non-failure of the inspection object in accordance with whether or not a defect has been detected. The display device 2 having received the determination signal displays a result of the determination.

An illumination substrate (illumination part) 15 is provided with the plurality of LEDs 11 for irradiating with light an imaged region where an inspection object is imaged, and a reflector (not shown) is provided in front of the LEDs 11. Further, the lens 12 is interchangeable as a lens unit for a short distance or a long distance.

The camera module ( ) 14 is provided with a focus adjustment mechanism for controlling the auto focus motion by rotation of the motor 141, and images the inspection object in accordance with an imaging instruction signal from the main substrate 13. In the present embodiment, a CMOS substrate 142 is provided as an imaging element, and an imaged color image is converted to an HDR image based on a conversion characteristic for expanding a dynamic range on the CMOS substrate 142, and is outputted to an FPGA 131 of the main substrate 13.

Figure 4:
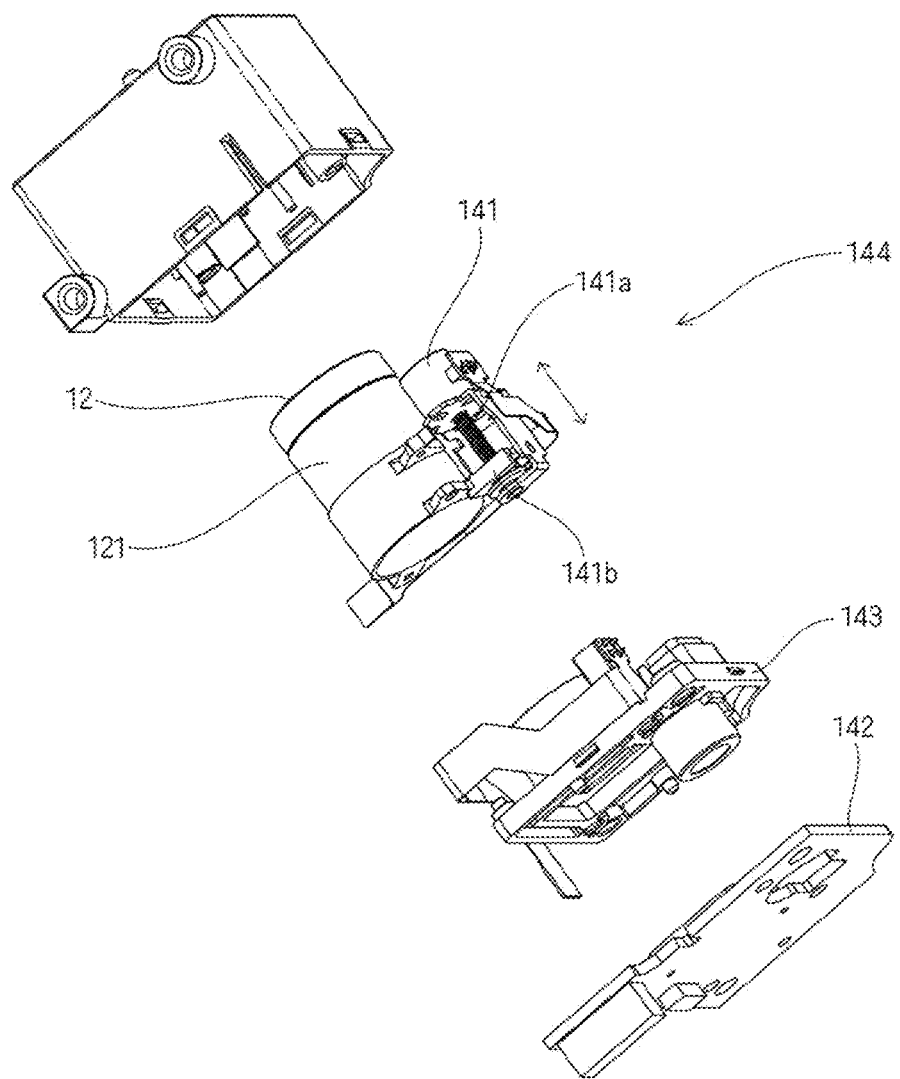
FIG. 4 is a perspective view showing a configuration of a focus adjustment mechanism of a camera module in the imaging device of the image processing sensor according to the embodiment of the present invention.

FIG. 4 is a perspective view showing a configuration of the focus adjustment mechanism of the camera module 14 in the imaging device 1 of the image processing sensor according to the embodiment of the present invention. As shown in FIG. 4, a base mount 143 is mounted on the CMOS substrate 142 of the camera module 14. The base mount 143 is provided with a vertical detection sensor (not illustrated) that detects motion in a vertical direction (arrow direction) of a lens support 121 that supports the lens 12 in a lens holder 144, and a rotation detection sensor (not illustrated) that detects rotation of the motor 141 as part of a mechanism to move the lens support 121.

The base mount 143 is mounted with the lens holder 144 configured by the lens support 121 and the mechanism to move the lens support 121. As shown in FIG. 4, an external thread is formed at a rotational shaft (screw mechanism) 141a of the motor 141, and is screwed with an internal thread formed at a nut (screw mechanism) 141b. Hence, the nut 141b linearly moves in the arrow direction in accordance with the rotation of the motor 141. The nut 141b is arranged so as to push up the lens support 121 from below, and the lens support 121 is pushed down to below by a biasing member (not shown). Accordingly, by controlling a reciprocating motion in the arrow direction of the nut 141b by rotation of the motor 141, the lens support 121 can be raised or lowered against the biasing force of the biasing member by means of the nut 141b, whereby a distance between the lens 12 provided in the lens support 121 and the inspection object can be adjusted.

Returning to FIG. 3, the main substrate 13 controls a motion of each substrate having been connected therewith. For example, with respect to the illumination substrate 15, a control signal for controlling turning-on/off of the plurality of LEDs 11 is transmitted to an LED driver 151. The LED driver 151, for example, adjusts turning on/off, an amount of light, and the like, of the LEDs 11 in accordance with the control signal from the FPGA 131. Further, a control signal for controlling an auto focus motion is transmitted to the motor 141 of the camera module 14 via a motor driver 181 of the power substrate 18, and an imaging instruction signal or the like is transmitted to the CMOS substrate 142.

While performing illumination control and imaging control, the FPGA 131 of the main substrate 13 executes image processing on the acquired image data (image processing unit). Further, a DSP 132 of the main substrate 13 executes edge detection processing, pattern search processing, and the like on the image data. As a result of the pattern search processing, an OK/NG signal (determination signal), indicating failure/non-failure of the inspection object in accordance with whether or not a defect has been detected is outputted to the communication substrate 17. A result of the arithmetic processing and the like are stored into a memory 133. Although the FPGA 131 executes illumination control, imaging control, and the like in the present embodiment, the DSP 132 may execute the illumination control, the imaging control, and the like. Further, a circuit formed of the FPGA 131 united with the DSP 132, namely a main control circuit (main control unit), may be provided. In short, the main control unit transmits the control signal for controlling turning-on/off of the plurality of LEDs 11 to the LED driver 151, transmits the control signal for controlling an auto focus motion to the motor 141 of the camera module 14 via the motor driver 181 of the power substrate 18, transmits the imaging instruction signal or the like to the CMOS substrate 142, and thus has both functions of the FPGA 131 and the DSP 132.

Figure 5:
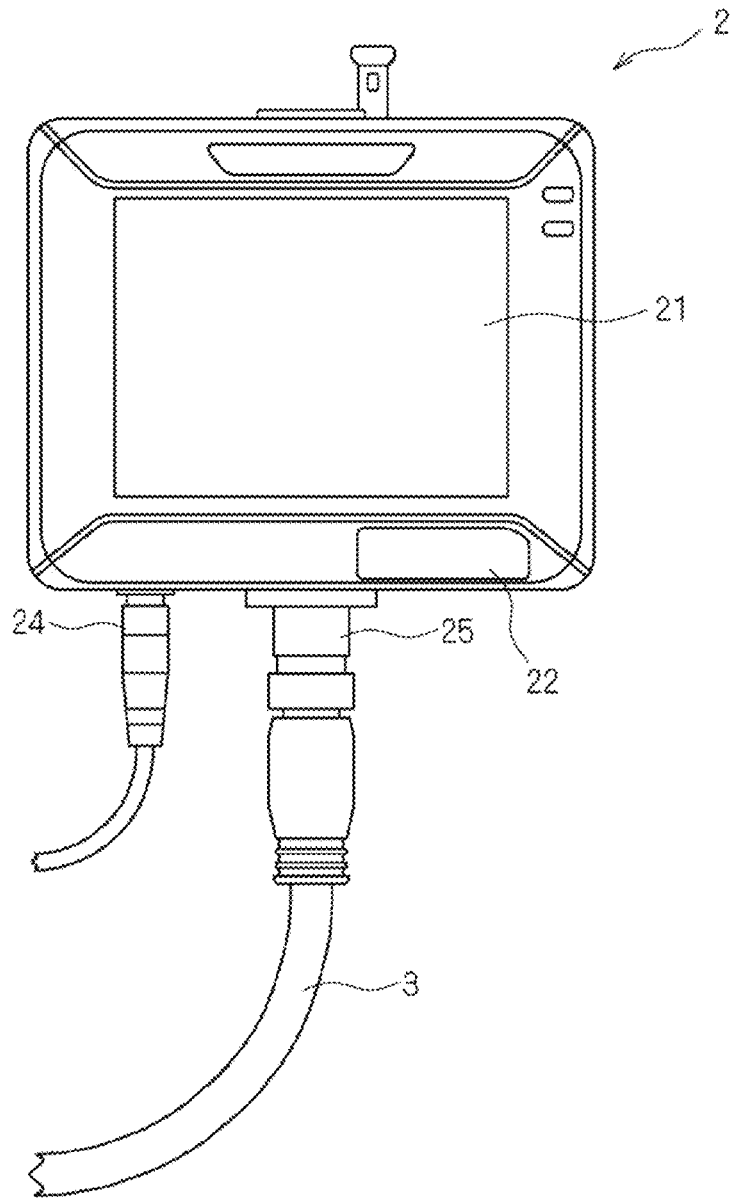
FIG. 5 is a front view showing a configuration of a display device of the image processing sensor according to the embodiment of the present invention.

FIG. 5 is a front view showing a configuration of the display device 2 of the image processing sensor according to the embodiment of the present invention. As shown in FIG. 5, a touch panel 21 is provided at the center portion of the front face of the display device 2, and displays a color image of an imaged inspection object on the screen, while accepting a selection input by the user.

Further, the display device 2 is provided with a power connector 24 to be connected with the power cable supplied with electric power from the external power source, and a power connector 25 connectable with the connection cable 3 that performs data communication with the imaging device 1. Moreover, a USB port 22 connectable with a USB memory and the like is provided on the front face.

Figure 6A:
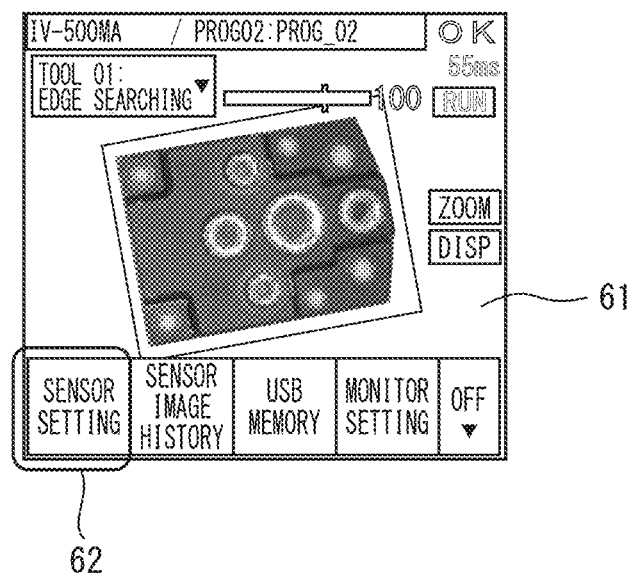
FIGS. 6A and 6B are exemplary views of mode switching screens in the display device of the image processing sensor according to the embodiment of the present invention.
Figure 6B:
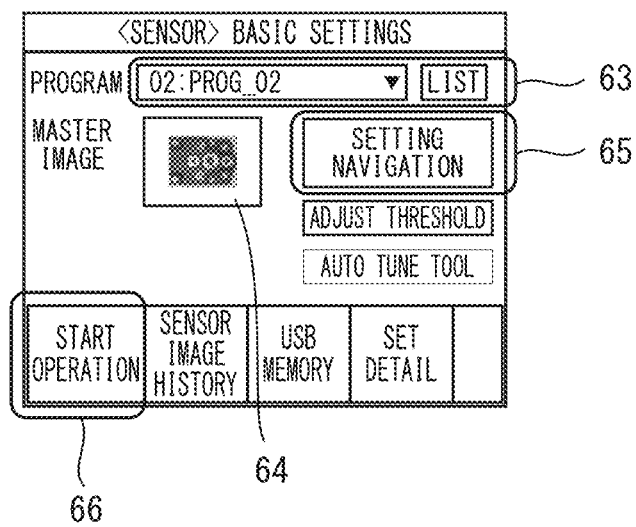

The user selects a button displayed on the screen of the touch panel 21 of the display device 2, to thereby control an operation of the image processing sensor. It is also possible to switch between "inspection mode" for executing an inspection of the inspection object and "setting mode" for performing a condition setting for the imaging device 1. In other words, the image processing sensor according to the present embodiment has a mode switching part for switching between the inspection mode (Run mode) for determining failure/non-failure of the inspection object and the setting mode (Non-Run mode) for setting a variety of parameters (imaging parameter, illumination parameter, image processing parameter, and the like) which are used for the inspection. FIGS. 6A and 6B are exemplary views of mode switching screens in the display device 2 of the image processing sensor according to the embodiment of the present invention.

FIG. 6A is an exemplary view of a screen display of "inspection mode". As shown in FIG. 6A, an image of the inspection object imaged by the imaging device 1 is displayed in an inspection object displaying region 61. A "SENSOR SETTING" button 62 at the lower left functions as the switching part, and when the "SENSOR SETTING" button 62 is selected, the mode is switched to "setting mode", and the screen transitions to the screen shown in FIG. 6B.

FIG. 6B is an exemplary view of a screen display of "setting mode". As shown in FIG. 6B, the kind of the inspection object or an inspection environment is selected in a program selecting region 63. Herein, the "program" means a series of data groups (combination of parameter values) set in accordance with the kind of the inspection object or the inspection environment, and a different data group can be stored as the program with respect to each kind of the inspection object or the inspection environment. Inspection condition data concerning a condition for inspecting the inspection object includes focus position data indicating a focalized position in the case of performing focus adjustment.

Further, when a master image as a typical image to become a reference for comparison with the inspection object is stored, the master image is displayed in a master image displaying region 64. When a "SETTING NAVIGATION" button 65 is selected, the screen transitions to a setting screen for performing detailed setting. A "START OPERATION" button 66 of FIG. 6B functions as the mode switching part, and when the "START OPERATION" button 66 is selected, the mode is switched to the "inspection mode", and the screen transitions to the screen shown in FIG. 6A.

Figure 7A:
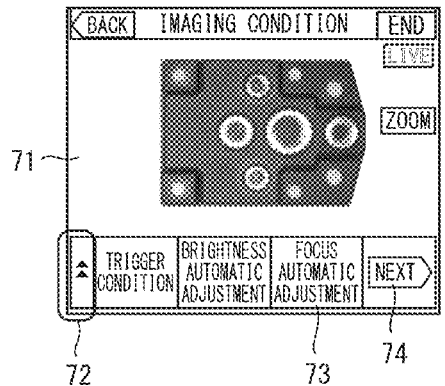
FIGS. 7A to 7F are exemplary views of setting screens in the display device of the image processing sensor according to the embodiment of the present invention.
Figure 7B:
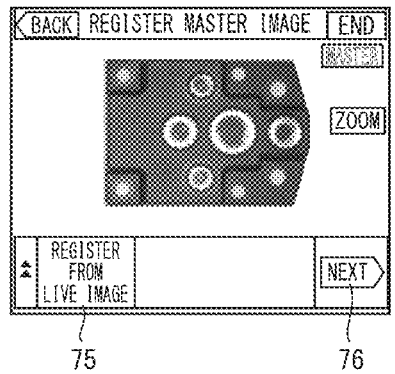
Figure 7C:
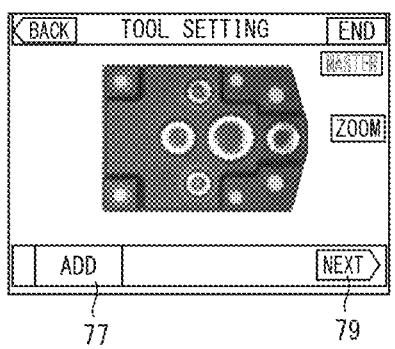
Figure 7D:
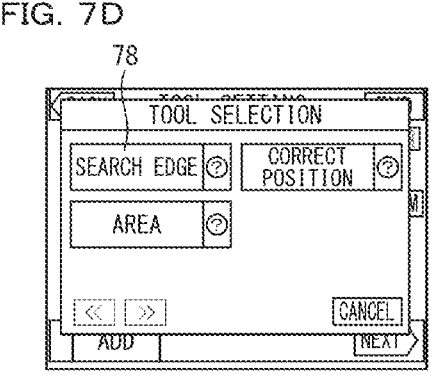
Figure 7E:
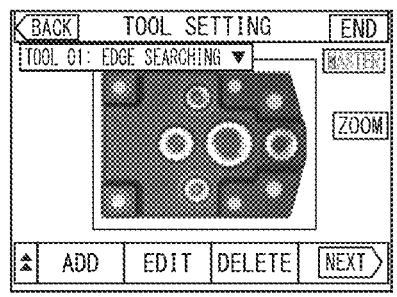
Figure 7F:
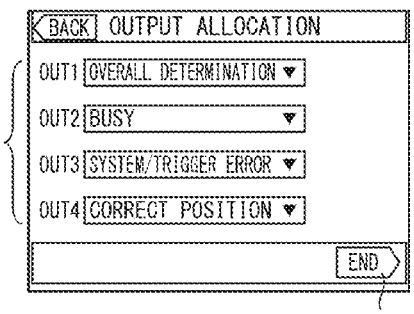

FIGS. 7A to 7F are exemplary views of setting screens in the display device 2 of the image processing sensor according to the embodiment of the present invention. Through the setting screens shown in FIGS. 7A to 7F, the user sequentially performs setting in the flow of setting of the imaging condition (FIG. 7A), registration of the master image to become a reference for pattern search (FIG. 7B), setting of a tool such as edge search on the master image (FIGS. 7C to 7E), and allocation of an output (FIG. 7F). Hereinafter, a detailed description will be given. When the "SETTING NAVIGATION" button 65 shown in FIG. 6B is selected, first, an imaging condition setting screen shown in FIG. 7A is displayed. On the imaging condition setting screen, a currently imaged image of the inspection object is displayed when the master image is not stored, and the master image is displayed in a main display region 71 when the master image is stored, and a setting button group for setting imaging conditions is displayed in the lower part of the screen. For example, when a "TRIGGER CONDITION" button is selected, it is possible to set a trigger condition for specifying a timing when the imaging device 1 images the inspection object. Although a detailed setting screen is omitted, when each button is selected, the setting screen is displayed on the touch panel 21 shown in FIG. 5 in accordance with each setting condition. The case where a "FOCUS AUTOMATIC ADJUSTMENT" button 73 is selected will be described later.

Further, for more detailed setting, an "EXTENDED FUNCTION" button 72 of FIG. 7A may be selected. When the "EXTENDED FUNCTION" button 72 is selected, a button for performing detailed setting is separately displayed. As described above, on the imaging condition setting screen, it is possible to adjust brightness, adjust focus, and set an imaging range, on/off of illumination, on/off of zooming, and the like. Focus adjustment will be described later.

When a "screen transition" button 74 displayed as "NEXT" of FIG. 7A is selected, a master image registering screen shown in FIG. 7B is displayed. Hereinafter, a variety of tools for inspection will be set on the registered master image. A plurality of programs can be stored with respect to one master image. That is, different tools can be set with respect to the same master image, and can be previously stored as different programs.

As the master image, an image of the currently imaged inspection object may be registered, or an image selected from previously imaged images may be registered. In the case of registering the currently imaged image, the user may select a "REGISTER LIVE IMAGE" button 75. An image being imaged at the time of selection of the "REGISTER LIVE IMAGE" button 75 is registered as the master image.

When a "screen transition" button 76 displayed as "NEXT" of FIG. 7B is selected, a tool setting screen for each master image, shown in FIG. 7C, is displayed. Hereinafter, a variety of tools for inspection will be set on the master image.

On the tool setting screen, a tool for executing the inspection is additionally set in the displayed master image. When an "ADD" button 77 shown in FIG. 7C is selected, a tool selecting screen shown in FIG. 7D is displayed. A tool selected on the tool selecting screen is additionally set. For example, when a "SEARCH EDGE" button 78 is selected, an edge search setting screen shown in FIG. 7E is displayed. By previously setting which edge of the master image is to be checked with the imaged image of the inspection object on the edge search setting screen, it is possible to determine failure/non-failure of the inspection object in accordance with whether or not a defect has been detected. Hereinafter, a color area, positional correction, and the like can be set.

When a "screen transition" button 79 displayed as "NEXT" of FIG. 7C is selected, an output allocating screen, shown in FIG. 7F, is displayed. On the output allocating screen, it is possible by selecting a setting button group 80 to set what an output line means, the line being displayed on the screen as a result of the inspection. When an "END" button 81 is selected, the screen display returns to "setting mode" shown in FIG. 6B. In this manner, by sequentially selecting the "screen transition" buttons 74, 76, 79 displayed as "NEXT" on the touch panel 21 of the display device 2 shown in FIG. 5, the user can easily set in a short period of time a variety of parameters which are used for the inspection. Further, since even a user who is not used to the image processing sensor is guided to a next operation on the touch panel 21 of the display device 2, a variety of parameters can be easily set.

In the present embodiment, inspection condition data in the case of performing focus adjustment is set and stored from the "setting mode" screen shown in FIG. 6B. The "SETTING NAVIGATION" button 65 is selected from the "setting mode" screen shown in FIG. 6B, and the imaging condition setting screen shown in FIG. 7A is displayed. The "FOCUS AUTOMATIC ADJUSTMENT" button 73 of FIG. 7A is selected, to perform focus adjustment.

Figure 8A:
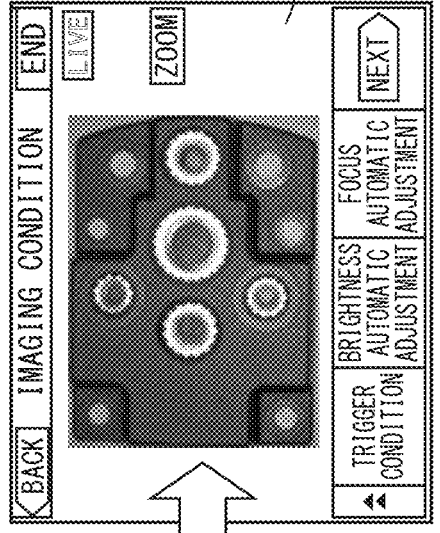
FIGS. 8A and 8B are exemplary views of a focus adjustment screen in the display device of the image processing sensor according to the embodiment of the present invention.
Figure 8B:
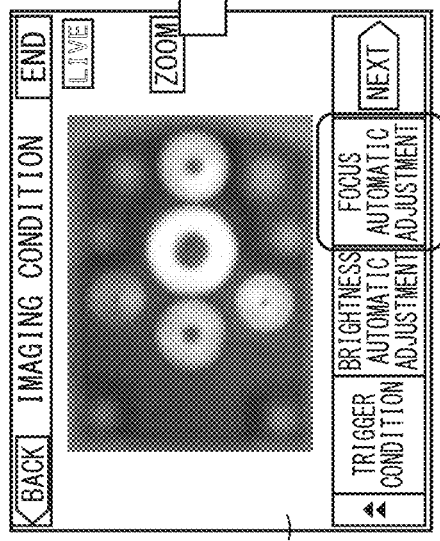

FIGS. 8A and 8B are exemplary views of a focus adjustment screen in the display device 2 of the image processing sensor according to the embodiment of the present invention. In FIG. 8A, a currently imaged image of the inspection object is displayed in the main display region 71. The "FOCUS AUTOMATIC ADJUSTMENT" button 73 is selected in this state to perform focus adjustment.

Specifically, at the time of selecting the "FOCUS AUTOMATIC ADJUSTMENT" button 73, the FPGA 131 transmits a control signal to the motor 141 of the camera module 14 to rotate the motor 141.

The lens 12 is moved from a position closest to the inspection object to a position farthest thereto, and the inspection object is imaged for a plurality of times so that the focalized position can be specified as the focus position as shown in 8B. The position specified as the focus position is, for example, set as "60". The FPGA 131 stores data as inspection condition data, which includes the specified focus position, the brightness of the focus position, setting of an output, and the like into the memory 133 by units of a program.

Figure 9:
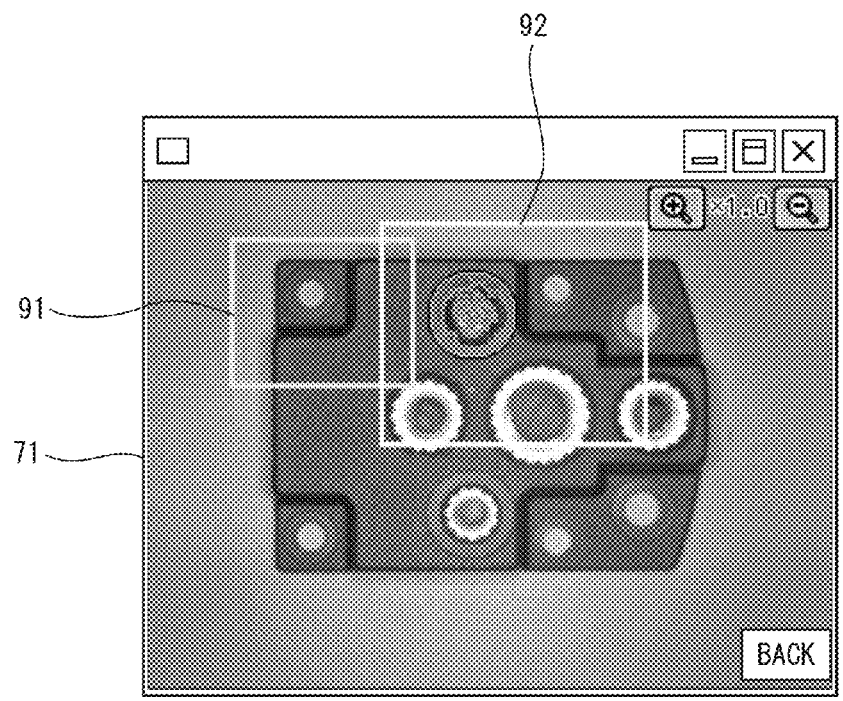
FIG. 9 is an exemplary view of a determination screen for presence or absence of a screw in the display device of the image processing sensor according to the embodiment of the present invention.

FIG. 9 is an exemplary view of a determination screen for the presence or absence of a screw in the display device 2 of the image processing sensor according to the embodiment of the present invention. In the main display region 71 of FIG. 9, a currently imaged image of the inspection object is displayed. In the example of FIG. 9, an inspection region 91 for a positional correction tool and an inspection region 92 for an edge discrimination tool are set.

FIG. 10 is a table showing a list of inspection condition data for the positional correction tool and the edge discrimination tool. As shown in FIG. 10, a variety of setting items are stored in association with setting examples. A data group as a combination of these setting items and setting examples is collectively stored as "PROGRAM 01" into the memory 133 shown in FIG. 3.

It should be noted that among the variety of setting items (setting parameters) shown in FIG. 10, as for trigger-related items, a parameter "Trigger system" for selecting at least any of an internal trigger and an external trigger is preferably set as an essential setting item. As for imaging related items, at least a parameter "BRIGHTNESS" for adjusting brightness of the screen and a parameter "AF ADJUSTMENT POSITION" for adjusting an auto focus position are preferably set as the essential setting items.

Further, as for tool related ones, a parameter "TOOL TYPE" for deciding at least what type of tool is to be used for performing the image processing and a parameter "THRESHOLD" (degree of agreement) to become a reference for the inspection accuracy are preferably set as the essential setting items. Especially, in the case of executing failure/non-failure determination for the inspection object, "TOOL TYPE" is preferably set as the essential setting item.

As described above, a plurality of setting items are included in one inspection condition data, and these plurality of setting items are made up, for example, of the setting item concerning the external output, the setting item concerning the trigger condition at least including "TRIGGER SYSTEM", the setting item concerning the imaging condition at least including "BRIGHTNESS" and "AF ADJUSTMENT POSITION", the setting item concerning illumination correction for deciding whether or not to perform illumination correction, the setting item concerning the presence or absence and specification of a master image, the setting item concerning the image processing tools at least including "TOOL TYPE", and the like.

Figure 11:
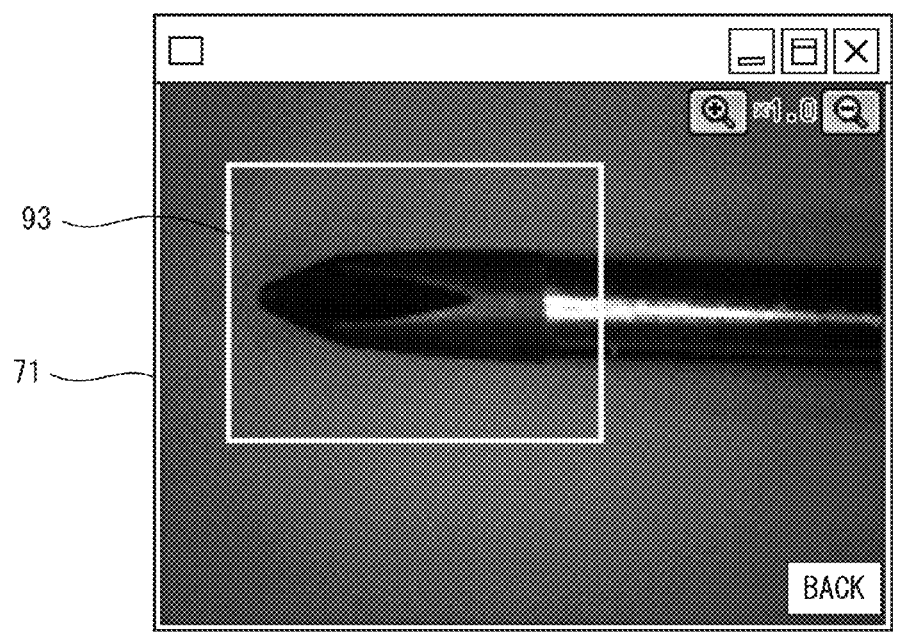
FIG. 11 is an exemplary view of a determination screen for a driver type of the display device of the image processing sensor according to the embodiment of the present invention.

FIG. 11 is an exemplary view of a determination screen for a driver type of the display device 2 of the image processing sensor according to the embodiment of the present invention. In the main display region 71 of FIG. 11, an image of a driver is displayed as a currently imaged image of the inspection object. In the example of FIG. 11, only an inspection region 93 of a color area tool is set.

FIG. 12 is a table showing a list of inspection condition data of the color area tool. As shown in FIG. 12, a variety of setting items which are different from those in FIG. 10 are stored in association with setting examples. A data group as a combination of these setting items and setting examples is collectively stored as "PROGRAM 02" into the memory 133 shown in FIG. 3.

Figure 13:
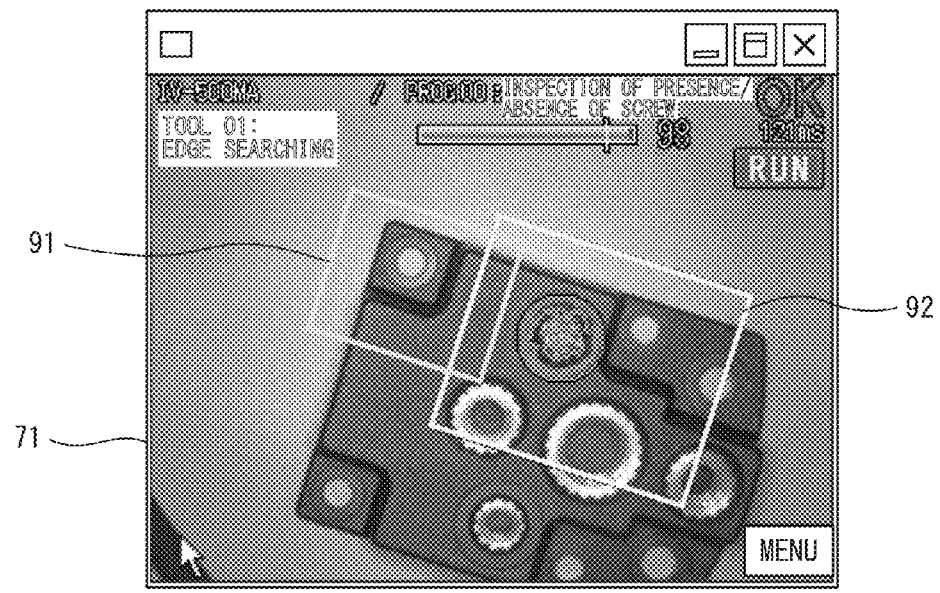
FIG. 13 is an exemplary view of an inspection screen for presence or absence of a screw in the display device of the image processing sensor according to the embodiment of the present invention.

"Switching the inspection condition data" means switching the data group stored with respect to each program. FIG. 13 is an exemplary view of an inspection screen for the presence or absence of a screw in the display device 2 of the image processing sensor according to the embodiment of the present invention. As shown in FIG. 13, when "PROGRAM 01" is selected as the inspection condition data, the inspection condition data shown in FIG. 10 is read, and while an image of the inspection object currently imaged in the main display region 71 is displayed, the inspection region 91 for the positional correction tool and the inspection region 92 for the edge discrimination tool based on the inspection condition data are displayed. FIG. 13 shows a result of determination that the screw is present in the inspection region 92. This has been devised to notify the user of the result by such a method of changing a color of a screw portion or generating a beeping sound.

Figure 14:
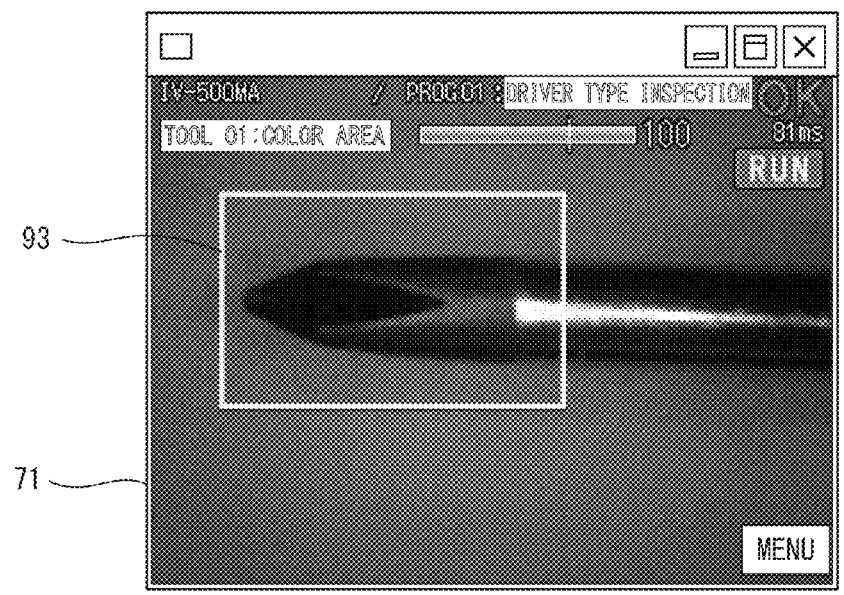
FIG. 14 is an exemplary view of a determination screen for a driver type in the display device of the image processing sensor according to the embodiment of the present invention.

Herein, when the program is switched from "PROGRAM 01" to "PROGRAM 02", the data group stored with respect to each program is switched to the inspection condition data of "PROGRAM 02" shown in FIG. 12. FIG. 14 is an exemplary view of a determination screen for a driver type in the display device 2 of the image processing sensor according to the embodiment of the present invention. In the example of FIG. 14, an image of the driver is displayed in the main display region 71, and it is determined that the tip is a black driver in the inspection region 93 of the color area tool. As described above, places of the inspection condition data is changed only by switching the program, and the inspection region corresponding to the tool included in the program is immediately set.

In such a manner, selecting "PROGRAM 01" or "PROGRAM 02" as the inspection condition data allows automatic performance of focus adjustment, thereby eliminating the need for taking the trouble of manually adjusting the focus and leading to significant alleviation of the trouble and time of the user. That is, in the image processing sensor (or display device 2), a plurality of pieces of different inspection condition data such as "PROGRAM 01" and "PROGRAM 02" are set and stored in the memory 133, and the user selects one inspection condition data by reading one inspection condition data out of these plurality of pieces of different inspection condition data from the memory 133.

The focus position is preferably held unchanged even when the program is switched. This is because, when the inspection object is an object having no problem with inspection even if the image is blurred due to slight displacement of a focal point, unnecessary focus adjustment is not required and the life of the focus adjustment mechanism can be extended.

Further, in the case of switching the program, movement to the focus position is sufficient when it is moved just for a difference between the focus position before switching the program and the focus position after switching the program. However, in order to prevent a loss of synchronization caused by repetition of focus adjustment, it is preferable that at the time of switching the program, the origin point of the focus position be corrected in line with an actual inspection object and the focus position be returned to the origin point, to move to a focus position specified by the program.

That is, the FPGA 131 upon receipt of a switching instruction for the program first performs correction of the origin point of the focus position. Information included in the inspection condition data, such as a shape and a size of the actual inspection object, is used for the correction. At the time of completion of the correction, the motor driver 181 is instructed to move the focus position to the origin point.

The FPGA 131 instructs the motor driver 181 to move the focus position to the position corresponding to the program after switching the program. This eliminates the need for performing image processing for specifying the focus position, and allows adjustment of the focus position only by operation of the focus adjustment mechanism based on the focus position data. Further, since the focus position has certainly been returned to the origin point, it is possible to prevent a loss of synchronization caused by successive focus adjustment.

As described above, according to the present embodiment, it is possible to perform focus adjustment only by switching the inspection condition data, which is made up of a plurality of setting items including focus position data, by the switching instruction for the inspection condition data, thereby eliminating the need for performing focus adjustment while changing the kind of the inspection object flowing along the manufacturing line once in a given period, and furthermore allowing focus adjustment to be performed in a relatively short period of time.

In addition, the present invention is not restricted to the above embodiment, and a variety of changes, modifications and the like can be made as long as it is within the scope of the gist of the present invention. For example, the imaging device 1 and the display device 2 are not limited to the form of being directly connected through the connection cable 3, and needless to say, the imaging device 1 and the display device 2 may be connected via a network such as LAN, WAN, or the like. Further, although the imaging device 1 and the display device 2 are separated bodies in this embodiment, the imaging device 1 and the display device 2 may be combined to form an image processing apparatus.

What is claimed is:

1. An image processing sensor, comprising:
   an imaging unit for acquiring a first image of a region including an inspection object;
   a focus adjustment mechanism for adjusting a focus position of the imaging unit on the inspection object;
   an image processing unit for executing image processing with the first image acquired by the imaging unit;
   an inspection condition data setting portion for setting a plurality of pieces of inspection condition data concerning a condition for inspecting the inspection object, each of the plurality of pieces of inspection condition data comprising a plurality of setting items including parameters used for image processing to be executed by the image processing unit and focus position data concerning an operation of the focus adjustment mechanism;
   a memory for storing the plurality of pieces of inspection condition data set by the inspection condition data setting portion;
   a control unit for controlling the operation of the focus adjustment mechanism based on focus position data included in a selected inspection condition data from the plurality of pieces of inspection condition data and for outputting an inspection result based on image processing with parameters included in the selected inspection condition data from the plurality of pieces of inspection condition data; and,
   an inspection condition switching instruction accepting portion for accepting a switching instruction for switching the selected inspection condition data to another inspection condition data to be selected; whereby,
   when the switching instruction is accepted by the inspection condition switching instruction accepting portion, the control unit controls the operation of the focus adjustment mechanism based on focus position data included in said another inspection condition data read from the memory and the image processing unit receives a second image acquired by the imaging unit based on the focus position data included in said another inspection condition data and executes image processing with the second image based on parameters included in said another inspection condition data read from the memory.

2. The image processing apparatus according to claim 1, further comprising a switching portion for switching between whether to execute processing for setting the inspection condition data or to execute processing for determining failure/non-failure of the inspection object.

3. The image processing apparatus according to claim 2, wherein the inspection condition data setting portion accepts an input from the user to set focus position data when switching is performed so as to execute the processing for setting the inspection condition data, and the control unit controls the operation of the focus adjustment mechanism so that the focus position becomes a position corresponding to the focus position data included in another inspection condition data after switching when switching is performed so as to execute the processing for determining failure/non-failure of the inspection object.

4. The image processing apparatus according to claim 1, wherein, when the switching instruction for the inspection condition data is accepted in the inspection condition switching instruction accepting portion, the control unit performs control so as not to change the focus position.

5. The image processing apparatus according to claim 1, wherein the focus adjustment mechanism is configured by a motor and a screw mechanism interlocked with rotation of the motor.

6. The image processing apparatus according to claim 5, wherein, when the switching instruction for the inspection condition data is accepted in the inspection condition switching instruction accepting portion, the control unit returns the focus position to the origin point and controls the rotation of the motor in accordance with the accepted switching instruction.

7. The image processing apparatus according to claim 6, wherein the inspection condition data includes information for correcting the origin point.

8. The image processing apparatus according to claim 1, wherein a typical image of the inspection object to become a reference for comparison with the inspection object is previously stored as a master image, and the inspection condition data is set while the master image is displayed.

* * * * *